United States Patent [19]

Uhr et al.

[11] Patent Number: 4,792,447

[45] Date of Patent: Dec. 20, 1988

[54] ANTI-IMMUNOGLOBULIN TOXIN CONJUGATES USEFUL IN THE TREATMENT OF B CELL TUMORS

[75] Inventors: Jonathan W. Uhr; Ellen S. Vitetta, both of Dallas, Tex.

[73] Assignee: Board of Regents, The University of Texas System, Austin, Tex.

[21] Appl. No.: 498,754

[22] Filed: May 27, 1983

Related U.S. Application Data

[63] Continuation-in-part of Ser. No. 286,090, Jul. 23, 1981, abandoned.

[51] Int. Cl.$^4$ ............... A61K 39/395; A61K 39/44; C07K 15/00; C07K 17/00
[52] U.S. Cl. ............... 424/85.91; 530/387
[58] Field of Search ............... 424/85, 92, 87; 260/112 R; 435/172.2; 530/387

[56] References Cited

U.S. PATENT DOCUMENTS 4,350,626  9/1982  Masuho et al. ............... 424/177
4,359,457  11/1982  Neville, Jr. et al. ............... 424/85

OTHER PUBLICATIONS

Chemical Abstracts, vol. 89, Abstract No. 16740q, 1978.
Chemical Abstracts, vol. 93, Abstract No. 232191m, 1980.
Chemical Abstracts, vol. 94, Abstract No. 132084f, 1981.
Chemical Abstracts, vol. 95, Abstract No. 78306k, 1981.
A. Krolick, et al., In Vivo Therapy of a Murine B Cell Tumor (BCL$_1$) Using Antibody-Ricin A Chain Immunotoxins, J. Exp. Med., vol. 155, pp. 1979–1809, (1982).
K. A. Krolick, et al., Selective Killing of Leukemia Cells by Antibody-Toxin Conjugates: Implications for Autologous Bone Marrow Transplantation, Nature, vol. 295, pp. 604–605, (1982).
P. E. Thorpe, et al., Abrogation of the Non-Specific Toxicity of Abrin Conjugated to Anti-Lymphocyte Globulin, Clin. Exp. Immunol., 43, pp. 195–200, (1981).
H. E. Blythman, et al., Immunotoxins Hybrid Molecules of Monoclonal Antibodies and a Toxin Subunit Specifically Kill Tumor Cells, Nature, vol. 290, pp. 145, 6 (1981).
L. L. Lanier, et al., Mechanism of B Cell Lymphoma Immunotherapy with Passive Xenogeneic Anti-Idiotype Serum, J. of Immunol., vol. 125, No. 4, pp. 1730–1736, (1980).
T. J. Hamblin, et al., Preliminary Experience in Treating Lymphocytic Leukemia with Antibody to Immunoglobulin Idiotypes on the Cell Surfaces, Br. J. Cancer, 42, pp. 495–502, (1980).
P. C. Isakson, et al., The Effect of Anti-Immunoglobulin Antibodies on the In Vitro Proliferation and Differentiation of Normal and Neoplastic Murine B Cells, J. of Immunol., vol. 125, No. 2, pp. 886–892, (1980).
F. K. Stevenson, et al., Extra Cellular Idiotypic Immunoglobulin Arising from Human Leukemic B Lymphocytes, J. Exp. Med., vol. 152, pp. 1484–1496, (1980).
E. S. Vitetta, et al., Characterization of the Spontaneous Murine B Cell Leukemia (BCL$_1$), III. Evidence for Monoclonality by Using an Anti-Idiotype Antibody, J. of Immunol., vol. 122, No. 5, pp. 1649–1654, (1979).
T. Ghose, et al., Antibody-Linked Cytotoxic Agents in the Treatment of Cancer: Current Status and Future Prospects, J. Natl. Cancer Inst., vol. 61, No. 3, pp. 657–676, (1978).
Michael Mulrhead, et al., "Increased Susceptibility to Lethal Effects of Bacterial Lipopolysaccharide in Mice with B-Cell Leukemia", JNCL, vol. 1, pp. 745–753, (1981).
Vic Raso, et al., "Specific Cytotoxicity of a Human Immunoglobulin Directed Fab'-Ricin A Chain Conjugate", Journal of Immunology, vol. 125, No. 6, (1980).
K. A. Krolick, et al., "Selective Killing of Normal or Neoplastic B Cells by Antibodies Coupled to the A Chain of Ricin", Proc. Natl. Acad. Sci. U.S.A., vol. 77, pp. 5419–5423, (1980).
D. Gary Gilliland, et al., "Antibody-Direct Cytotoxide Agents: Use of Monoclonal Antibody to Direct the Action of Toxin A Chains to Colorectal Carcinoma Cells", Proc. Natl. Acad. Sci., vol. 77, pp. 4539–4543, (1980).
Dorothy Yuan, et al., "A Peptide Difference Between the $\mu$-Chains from Cell-Associated and Secreted IgM of the BCL$_1$ Tumor", Journal of Immunology, vol. 125, pp. 40–45, (1980).
Peter Isakson, et al., "Acquisition of Cell Surface IgD After In Vitro Culture of Neoplastic B Cells from the Murine Tumor BCL", J. Exp. Med., vol. 151, pp. 749–754, (1980).
K. A. Krolick, et al., "Murine B Cell Leukemia (BCL$_1$): Organ Distribution and Kinetics of Growth as Determined by Fluorescence Analysis with an Anti-Idiotypic Antibody", Journal of Immunology, vol. 123, pp. 1928–1935, (1979).
Keith Krolick, et al., "BCL$_1$, a Murine Model for Chronic Lymphocytic Leukemia: Use of the Surface Immunoglobulin Idiotype for the Detection and Treatment of Tumor", Immunological Rev., vol. 48, pp. 81–106, (1979).

Primary Examiner—Blondel Hazel
Attorney, Agent, or Firm—Arnold, White & Durkee

[57] ABSTRACT

Highly specific antibodies directed against immunoglobulin determinants coupled to one or more toxin molecules provide antibody-toxin conjugates which are useful in selectively inhibiting the growth of target immunoglobulin generating cells. The antibody-toxin conjugate consists of an antibody specific for a selected immunoglobulin determinant including isotypic, allotypic or idiotypic variable determinants, coupled to one or more toxin molecules. Anti-idiotype toxin conjugates are provided which have specificity which distinguishes B cell tumor cells from normal B cells. Also disclosed is an antibody-toxin conjugate consisting of anti-IgD A chain. The antibody-toxin conjugate is used as a cell or tumor specific cytotoxic agent directed selectively against those cells expressing the corresponding immunoglobulin to which the antibody portion has specificity.

8 Claims, No Drawings

ANTI-IMMUNOGLOBULIN TOXIN CONJUGATES USEFUL IN THE TREATMENT OF B CELL TUMORS

BACKGROUND OF THE INVENTION

The present application is a continuation-in-part application of pending application Ser. No. 286,090, filed July 23, 1981, entitled "Antibody-Toxin Conjugates" now abandoned.

The present invention relates generally to immunotherapy agents; and more particularly, it relates to the antibody-toxin conjugates in which the antibody is specifically directed against immunoglobulin antigenic determinants including isotypes, allotypes and idiotypes. This invention also relaes to the use of such conjugates to deliver toxic agents to neoplastic B lymphomas or normal B cells that express certain immunoglobulin.

B cell tumors account for a significant proportion of human lymphoid tumors. About 75% of non-Hodgkins lymphomas and virtually all chronic lymphocytic leukemias (CLL) are of chronic lymphocytic leukemia there is a variant subset of the disease called prolymphocytic chronic lymphocytic leukemia. Notably, prolymphocytic CLL is a more acute disease characterized by massive splenomegaly and leukemia, with little or no invasion of lymph nodes. Furthermore, the disease is generally unresponsive to most chemotherapy regimens resulting in the most unfortunate consequence that the majority of patients survive less than 6 months after diagnosis.

Treatment of B cell lymphomas (solid tumors) and CLL is frequently unsatisfactory and prediction of the clinical course based on the histology of the tumors is unreliable. Thus, prior attempts to link clinical or cellular characteristics of the disease to prognosis and treatment have been met with difficulties.

Five modalities of therapy have been used during the past 30 years with varying degrees of success to control B cell tumors. The modes of therapy include: (a) radiation therapy, either total body or local radiation; (b) adrenal steroids; (c) alkylating agents; (d) combination therapy such as chlorambucil and prednisone; and (e) splenectomy. Complications due to current modes of tumor treatment often include anorexia, alopecia, severe nausea, ulceration of the intestinal tract, and enhanced susceptibity to infection. Moreover, the deaths related to complications of therapy are significant. For example, 16% of the deaths of patients diagnosed with CLL were attributed to complications of therapy. Thus, it can be appreciated that new modalities of therapy are highly desirable.

The possibility of utilizing the exquisite specificity of antibodies to direct cytotoxic agents to tumor cells has been considered since the studies of Ehrlich, *The Collected Papers of Paul Ehrlich*, ed. Himmelweit, F., Vol. 3 (Pergamon, Elsmford, N.Y. 1960). Studies using drug-antibody conjugates for this intended purpose have been hampered by the difficulty of raising antisera specific for tumor cells, the inability in preparing purified antibody for subsequent drug conjugation, and the problems of preserving both pharmacological and immunological activity after production of hybrid conjugate molecules. Several recent developments suggest that these obstacles can not be surmounted and that the technical expertise is now available for a reinvestigation of the above approach. First, the development of techniques for the generation of somatic cell hybrids secreting monoclonal antibody [See, for example, Kohler, et al, *Nature* 256: 495–497 (1975)] and successful application of affinity chromatography of conventional antisera make it possible to prepare usable concentrations of highly purified antibody.

Second, it has been demonstrated that the idiotype of the cell surface immunoglobulin of a B cell tumor represents a clonally expressible tumor specific marker [see Fu, et al, *J. Immunol* 114: 250–252 (1975)]. The idiotypic marker of the tumor B cell secreted antibody represents unique tumor-specific antigen which is capable of eliciting a corresponding anti-idiotype antibody.

Finally, many potent protein toxins such as ricin, abrin, and diphtheria toxin have been shown to consist of a toxin portion (A chain) covalently bound to a portion (B chain) that can bind to surface moieties on cells and thereby facilitate entry of the toxic peptide into the cell. [See for example, publications: Olsnes, S. and Pihl, A. *Receptors and Recognition*, ed. Cuatrecasas, P. Vol. 1, Series B, pp. 130–173 (Halstead, N.Y. 1976); Pappenheimer, et al, *Science* 182: 353–358 (1973)]. The internalized toxic peptide kills the cells by catalytic inhibition of protein synthesis. By substituting specific antibody for the B chain portion of the toxin molecule, it is possible to direct the toxic peptide of cells for which the antibody is specific.

Although the concept of constructing cytotoxic therapeutic agents by coupling highly toxic proteins, such as diphtheria toxin and ricin toxin, to antibodies is currently known in the art, antibody-toxin conjugates employing antibodies recognizing immunoglobulins virtually unique to B cells or more specifically to B cell tumors has not heretofore been accomplished.

There are a number of reports to the coupling of toxic polypeptides to lectins, hormones, and antibodies. Gilliland et al, *Proc. Nat'l. Acad. Sci. U.S.A.* 75: 5319–5323 (1978) coupled the A fragment of diphtheria toxin to concanavalin A. This conjugate was toxic but displayed the expected broad binding specificity associated with concanavalin A. Uehida et al, *J. Bio. Chem.* 253: 6307–6310 (1978) reported similar results using *Wistaria floribunda* lectin. Oeltmann et al, *J. Bio. Chem.* 254: 1022–1032 (1979) produced a conjugate between the A chain of ricin and human chorionic gonadotropin that showed a selective killing of cells bearing receptors for that hormone. Similarly, Chang et al, *J. Bio. Chem.* 252: 1515–1522 (1977) have reported the coupling of the A fragment of diphtheria toxin to human placental lactogen.

Conjugates have also been prepared between whole diphtheria toxin and antibodies directed against human lymphoblastoid cell lines and virus transformed hamster fibroblasts. These conjugates however were also cytotoxic for the corresponding non-neoplastic cell types. Most recently, Masuho, et al, *Biochem. Biophys. Res. Commun.* 90: 320–326 (1979) demonstrated that the Fab' fragments of an antibody directed against a murine leukemia (L1210) were cytotoxic for tumor cells when covalently associated with the A fragment of diphtheria toxin. In contrast, intact diphtheria toxin was not cytotoxic for the same cells, indicating the cells lacked either the toxin receptor or the ability to transmit the A fragment across the membrane.

SUMMARY OF THE INVENTION

This invention relates to an antibody-toxin conjugate having an antibody component directed against immunoglobulin determinants, said antibody component coupled to one or more toxin molecules. Such an antibody-toxin conjugate, as a cytotoxic agent specific for B cell lymphocytes is useful in the treatment of B cell tumors, including leukemia.

The present invention is distinguished from the above-referenced studies by the exploitation in the antibody-toxin conjugate of an antibody directed against immunoglobulin determinants, preferably IgD. The significance of employing an antibody directed against or specific for immunoglobulin is that b lymphocytes are responsible for the generation of immunoglobulin molecules and bear IgD. Therefore, an antibody-toxin conjugate of the present invention serves to deliver the toxic agent solely to cells which exhibit the particular immunoglobulin to which the antibody is directed, i.e. all or only a subset of B lymphocytes. Since immunoglobulin association is mainly on B lymphocytes, the antibody-toxin conjugate is targeted for these cells, while the remaining cells in the body, whether they be heart, lung, retina, kidney, bone, etc., which do not express immunoglobulin go unaffected by the antibody-toxin conjugate.

An even more elegant application of the present invention, is the utilization of an antibody directed against the idiotypic marker uniquely characterized of a B cell tumor generated immunoglobulin. Utilizing such an exquisitely specific antibody in the antibody-toxin conjugate serves to direct the conjugate to only those B cells which express the unique idiotype. In this fashion, the anti-idiotype toxin conjugate can pick one immunoglobulin molecule out of a population of maybe one million, and since the B cell tumor always comes from one particular lymphocyte population, they all express the same immunoglobulin idiotype. This anti-idiotype toxin conjugate will therefore react with the B cell tumor cells and not with other normal B cells.

Embodiments are discussed wherein antibody directed against immunoblobulin determinants, including isotypic, allotypic and idiotypic expressions, is covalently coupled to the A chain of ricin.

Also, embodiments are discussed wherein the antibody-toxin conjugates are used as cytotoxic agents in the exogenous and in vivo regression of B-cell tumors. Specifically, antibody toxin conjugates are provided which are useful for therapeutic intervention in the treatment of a mammalian host exhibitng a B cell tumor. The antibody toxin conjugates are effective in therapeutic intervention to promote the regression of B cell tumors.

The antibody-toxin conjugate contemplated by the present invention retains both the antigen-binding capacity of the antibody component and the toxic properties of the toxin component. Further, minute amounts of the conjugate are effective in inhibiting the growth of specific target cells expressing the complementary antigenic immunoglobulin.

DETAILED DESCRIPTION OF THE PREFERRED EMBODIMENT

In accordance with the present invention, antibodies directed against immunoglobulin determinants coupled to one or more toxin molecules provide a delivery system for toxic agents specific for target immunoglobulin generating cells. Such antibody-toxin conjugates combine the determinant specificity of antibody with the lethal effects of toxic agents thereby providing site-specific immunotherapeutic agents.

In accordance with the embodiments of this invention, an antibody is provided which directs its binding specificity against the antigenic determinants expressed by immunoglobulin molecules. Antibodies can be developed which are specific for the collective class of immunoglobulins by employing the specificity for the λ or κ light chain portion of an immunoglobulin, which light chains are common to all classes of immunoglobulin.

Moreover, antibodies can be developed which exhibit ever increasing selectivity toward antigenic distinct features of immunoglobulins. For example, immunoglobulins are divided into five principle isotypic classes labelled: IgA, IgD, IgE, IgG, and IgM. Correspondingly, antibodies can be developed which are specific for one isotypic class or subclasses thereof including H or L chain types but not reactive toward the other isotypes.

Even more discrete selectivity can be developed in antibodies which can distinguish between individuals of the same species. Such antibodies are specific for the allotypic determinant of immunoglobulins.

Finally there are antibodies which can distinguish and selectively react with a particular and unique immunoglobulin molecule or ones very closely related to it. Such an antibody is directed against an immunoglobulin idiotype. The specificity comes from the fact that a portion of immunoglobulin molecule called the variable portion differs between different immunoglobulin molecules of the same isotype and allotype. Idiotypes are unique to immunoglobulin molecules produced by given clone of immunoglobulin producing cells.

As contemplated by the present invention, the antibody-toxin conjugate preferably consists of the entire antibody molecule, however, the antibody can suitably be a fragment of the antibody molecule. The fragment desirably retains the immunochemical specificity and reactivity characteristic of the whole antibody. Such fragments are the so called Fab'2, Fab', Fab and Fv fragments.

Further, in accordance with the preferred embodiments of the present invention, one or more toxin molecules are coupled to the antibody or antibody fragment provided. As used in the context of this invention, the term "toxin" is used herein to include the commonly designated toxins such as poisonous lectins, ricin, abrin, modeccin, botulina and diphtheria toxins or preferably the toxic A chain portions thereof, as well as other toxic agents such as radioisotopes, cytotoxic and carcinostatic drugs. Combinations of the various toxins can also be coupled to one antibody molecule thereby accomodating variable cytotoxicity.

The coupling of one or more toxin molecules to the antibody is envisioned to include many chemical mechanisms, for instance covalent binding, affinity binding, intercalation, coordinate binding, and complexation. The preferred binding is, however, covalent binding. The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

Further in accordance with the present invention, a method of inhibiting the growth of immunoglobulin generating cells present in tissue samples and in vivo host systems is provided which involves the administration of an antibody-toxin conjugate to the tissue sample or host system.

In particular, it is contemplated that the antibody-toxin conjugates of this invention are useful in the therapeutic intervention of B-cell tumors. According to one such preferred application, the antibody component of the conjugate is directed against a variable determinant, idiotype, of an immunoglobulin molecule generated by the B-cell tumor. Such an antibody coupled with toxin molecules when introduced to tissue samples or a host system will selectively combine with the specific surface immunoglobulin of the tumor cell but will not bind to the surface of virtually all other cells present in the tissue sample or host system whether that cell be B cells or otherwise. Hence, this antibody directed against the immunoglobulin variable region determinant can specifically and selectively deliver the coupled toxic drug to such tumor cells which manufacture the target immunoglobulin.

According to another preferred embodiment of the invention useful for the therapeutic treatment of B-cell tumors, the antibody component of the component of the conjugate is directed against the isotypic class of immunoglobulin, IgD. Anti-IgD toxin conjugate is a surprisingly effective in vivo agent for treating B-cell tumors. Anti-IgD immunotoxin, in contrast to anti-idiotype immunotoxin can be viewed as a potentially universal immunotoxin for the management of B-cell tumors. The success of anti-IgD toxin conjugate as an in vivo therapeutic agent can be in retrospect attributed to the several factors including: (a) large amounts of anti-IgD can be raised either by immune sera or monoclonal antibody techniques; (b) B-cell tumors as well as normal B cells, bear IgD; (c) serum IgD levels in most mammals are extremely low; and (d) although IgD bearing normal B cells are virtually eliminated after treatment, immature B cells lacking IgD, or stem cells should repopulate the B cell compartment after the elimination of mature IgD bearing B cells.

To illustrate the manufacture and use of antibody-toxin conjugates directed against B-cell associated antibodies, five examples will be described. The first example involves the preparation and use of an anti-idiotype ricin A conjugate directed against a B cell tumor. The second examples describe the preparation and ue of an anti-isotype directed against mouse IgM coupled to ricin A chain. The third examples illustrates the implementation of anti-allotype directed against one allolic determinant of mouse IgD coupled with ricin A chain. The fourth example demonstrates the use of anti-idiotype toxin conjugate in the therapeutic intervention of B cell tumors, wherein the anti-idiotype toxin conjugate is a selective cytotoxic agent specific for B cell tumors. The fifth examples illustrates the therapeutic intervention of B cell tumor growth using an anti-IgD toxin conjugate. The anti-IgD toxin is effective in eliminating B cells bearing IgD, tumor cells as well as normal B cells. The examples which follow should not be construed to limit the scope of the invention, but rather serve to illustrate the best mode known to the inventors at the time of this application.

EXAMPLE I

Preparation of Anti-idiotype Specific for IgM Expressed by $BCL_1$ Tumor Cells

The $BCL_1$ tumor, described by Slavin et al, *Nature* 272: 624 (1977), is a monoclonal murine B cell leukemia that resembles B-CLL in the human. Because the $BCL_1$ tumor cells produce but do not secrete immunoglobulins it was necessary to hybridize these cells with myeloma cells in order to generate a cell line hybridoma capable of secreting immunoglobulin. In particular, the hybridoma secreted immunoglobulin, IgM, expressing a $BCL_1$ idiotype. This $BCL_1$ idiotype was produced in sufficient quanity and purity to provide an affinity basis for the purification of the anti-idiotype antibody.

BALB/c mice were obtained from Cumberland View Farms, Clinton, Tenn. The $BCL_1$ tumor was maintained in vivo by intravenous passage of $10^6$ spleen cells obtained from a $BCL_1$ tumor bearing mouse [(see Vitetta et al, *J. Immunol.* 122: 1649 (1979)].

Spleens from tumor bearing animals were removed four to eight weeks after inoculation with tumor cells, teased into balanced salt solution and washed twice. The $BCL_1$ cells were then cultured for 24 hours with lipopolysaccharide, *Salmonella typhosa* 0901 (Difco Laboratories, Detroit, Mich.) in RPMI 1640 (Grand island Biologicals, Grand Island, N.Y.). The culture medium was supplemented with the lipopolysaccharide at 50 $\mu$g/ml.

P3/x63-Ag8 myeloma cells [Krolick et al, *Proc. Nat'l. Acad. Sci. USA* 77: 5419 (1980)] and the stimulated $BCL_1$ tumor cells were fused in the presence of polyethylene glycol. The production of this hybridoma was done according to the standard procedure of Kohler et al, *Nature* 256: 495 (1975). The hybridoma secrete IgM$\lambda$ which is the original cell surface IgM of the $BCL_1$ line.

After the addition of polyethylene glycol, the cells were centrifuged for 4.5 minutes at 400$\times$g and the hybridization was terminated at 6 minutes. The hybridized cells were suspended in media containing 5$\times 10^7$ fresh BALB/c splenocytes per ml. Cells were distributed into 96-well microculture plates (Falcon) and incubagted at 37° C. in a 5% $CO_2$ atmosphere. Culture medium containing aminopterin was first added 24 hours after hybridization. Colonies of hybrid cells were visible microscopically by eight days after hybridization.

In order to determine whether a particular clone secreted IgM$\lambda$, culture supernatant was transferred in duplicate to the wells of an assay plate coated with affinity-purified rabbit anti-mouse $\mu$ heavy chain (RAM$\mu$). [RAM$\mu$ was prepared according to methods presented in Isakson et al, *J. Immunol.* 125: 886–892 (1980)]. Next, the well contents were exposed to $^{125}$I-rabbit anti-mouse $\lambda$ light chain. Radioactivity bound to the wells was then compared to that of wells in which standard control proteins were substituted for culture fluid. The amount of IgM$\lambda$ present in the wells was proportional to the amount of bound radioactivity detected on the well surface.

IgM$\lambda$ positive clones were transferred to larger vessels and were adapted to grow in culture on Dulbecco's modified Eagle's medium supplemented with 10% fetal calf serum. To demonstrate which hybridomas secreted IgM$\lambda$ expressing the $BCL_1$ idiotype, cells were then incubated with [$^3$H]-leucine. The radioactive secreted immunoglobulins were analyzed by immunoprecipitation and polyacrylamide gel electrophoresis. [See Applicant's paper, KZolick et al, *Proc. Nat'l. Acad. Sci. USA* 77: 5419-5423 (1980) for determination of $BCL_1$ idiotype positive hybridoma].

The hybridomas that secreted an idiotype-positive $IgM_\lambda$ were weaned in normal medium and propagated in Spinner culture. Following a period of maintenance in continuous culture, the hybrid tumor cells were injected into mineral oil primed BALB/c mice to grown as an ascites in the peritoneal cavity. The ascites were collected 10-15 days later.

The IgM was purified from both the tissue culture supernatant and the ascites of the mice by a combination of 50% saturation with ammonium sulfate to yield a immunoglobulin precipitate followed by chromatography on Biogel ACA-34 to separate IgM from IgG. The purity of the IgM preparation was tested by immunoprecipitation and SDS-polyacrylamide gel electrophoresis, according to the standard procedures of Weir, D. M., *Handbood of Experimental Immunology* 3rd ed. p. 639 (1978).

The purified IgM was used to stimulate production of rabbit anti-idiotype. New Zealand white adult rabbits were immunized with 100 μg of the purified mouse IgM, emulsified in Freund's complete adjuvant. The rabbits were injected in the four footpads and subcutaneously along the back. The rabbits received 100 μg boosters of the antigen, IgM, four weeks later and then bled at intervals of between one week and one year later. When the titers of immunoglobulin production dropped, the rabbits received additional boosters of 100 μg IgM in complete Freund's adjuvant.

The antibody against mouse IgM was first purified on a column of Sepharose bound to the $BCL_1$-$IgM_\lambda$ isolated from the ascites of BALB/c mice inoculated with $BCL_1$-P3/X63-Ag8 hybridoma cells. The antibody was eluted from the column with 3.5M $MgCl_2$, dialyzed, concentrated, and adsorbed sequentially with Sepharose bound to mouse euglobulin, myeloma proteins: MOPC-21 protein ($\gamma,\kappa$); TEPC-183 protein ($\mu,\kappa$), MOPC-315 protein ($\alpha,\lambda$), and paraformaldehyde-fixed BALB/c spleen cells. These purification stpes were performed to remove all activity against $\mu$, $\kappa$, $\lambda$, and $\alpha$ chains. The resulting preparation of antiserum was specific for the $BCL_1$ idiotype. The idiotype specificity was tested by indirect fluorescence analysis of $BCL_1$ tumor cells and control normal BALB/c spleen using a fluorescence activated cell sorter, a technique described in Vitetta et al, *J. Immunol.* 122: 1649-1654 (1979). This analysis indicated no binding of anti-idiotype to normal spleen cells but intense staining of anti-idiotype to tumor cells was evident.

Preparation of Anti-Idiotype Ricin A Conjugate

A ricin molecule is composed of a cytotoxic (A) chain and a binding (B) chain associated by a disulfide bond. The A chain from *Ricinus communis* agglutinin II (purchased from Vector Laboratories, Burlington, CA) was isolated after reduction of the disulfide bonds by ion-exchange chromatography following the procedures of Olsnes et al, *Biochemistry* 12: 3121-3126 (1973). Ricin A chain was concentrated by vacuum dialysis against 10 mM phosphate-buffered saline pH 7.0, containing 0.05% 2-mercaptoethanol.

In a seprate vessel, thiol groups were introduced onto affinity-purified anti-idiotype by adding 100 μg of the antibody in 250 μl phosphate buffered saline, pH 7.0, to 1.3 μl of 0.1% ethanolic N-succinimidyl 1-3-(3-pyridlyldithio)propionate (Pharmacia). This reaction mixture was incubated for 30 minutes at room temperature, after which the time the mixture was dialyzed against acetate buffer, 100 mM, pH 4.5, for two hours at room temperature. After introduction of the 2-pyridyldisulfide groups onto the anti-idiotype protein, free sulfhydryl groups were generated by reduction in 5 mM dithiothreitol at ambient room temperature for 30 minutes.

To covalently bond the ricin A chain to the anti-idiotype, a five fold molar excess of ricin A chain was mixed with the thiolated antibodies. The mixture was dialyzed extensively against 10 mM phosphate buffered saline, pH 7.0. The antibody-toxin conjugate was further purified by chromatography on sephacryl 200 in phosphate buffered saline. The first fall through peak (which represents the conjugate) was pooled and stored at 4° C. The anti-idiotype ricin A chain conjugate tends to aggregate and was, therefore, used within five days.

Treatment of Cells with Anti-Idiotype Ricin A Chain Conjugates

The optimal dose of each conjugate directed against a target cell line was determined by titration. This was done by diluting the conjugate, anti-idiotype ricin A, 1:2, 1:5, 1:10, 1:20, and 1:100. Each dilution of antibody toxin conjugate was evaluated for its effect on protein synthesis of the target cells, the B cell tumor lymphocytes.

To evaluate the immunotherapeutic potential of the formed anti-idiotype ricin a chain conjugate, the conjugate was cultured in combination with target cells: normal B cells, $BCL_1$ tumor cells, and two unrelated tumors, CHl and ASL-1.

Previous studies on the mechanisms of action of ricin have indicated that protein synthesis is irreversibly and catalytically inhibited in treated cells, thereby leading to cell death [see Olsnes et al, *Receptors and Recognition*, Ed. Cuatrecasas, P., Series B, Vol. 1, pp. 130-173 (Halsted, N.Y. 1976)]. In the following studies, inhibition of protein synthesis was used as an indicator of cell death.

Spleens selected from normal 2- to 4-month old BALB/c of C57BL/6 mice (Cumberland Farms, Clinton, TN) or from tumor cell bearing mice, $BCL_1$, CHl, ASL-1 tumors, were teased into suspension as a single-cell culture of the respective tissue in a balanced salt solution containing 0.05% fetal calf serum.

Aliquots of $10^7$ target cells were treated at 4° C. for 15 minutes with with 10 μl of 1-20 mg/ml of the appropriate experimental or control conjugates. The experimental conjugate was the anti-idiotype ricin A conjugate described in the section above. The control conjugate was normal rabbit immunoglobulin (NRIg) covalently bound with ricin A chain. Further, the effect of unconjugated anti-idiotype directed against $BCL_1$ tumor cells was tested for its effect on both normal and tumor cells.

After exposure of the target cells to the experimental or control conjugate or unconjugated anti-idiotype, the cells were spun down in a centrifuge followed by two subsequent washes.

After centrifugation each well received 20 μl of Hepesbuffered RPMI 1640 medium (Gibco) supplemented with gentamycin at 10 μg/ml, 2 mM glutamine, 5% fetal calf serum (Gibco), and 50 μM 2-mercaptoethanol. In addition, the B lymphocyte mitogen lipopolysaccharide (*Salmonella typhosa* 0901) (Difco) was added to a final concentration of 50 μg/ml. The cells were cultured at 37° C. in a 10% $CO_2$ atmosphere.

After 48 hours, each well received 1μ Ci of [³H]-leucine (25 Ci/mmol; New England Nuclear) and incubation was continued for an additional 16 hours. Following this incubation, the cells were harvested from the wells with a multiple automated cell harvester (MASH II; Microbiological Associates, Bethesda, MD.). The incorporation of [³H] leucine into protein which represents cell viability was determined in a Beckman LS-330 scintillation counter.

The results of treating tumor cells and normal cells with the experimental and control conjugates are tabulated below. The results are presented as percentage of [³H] leucine incorporation in sample cells relative to untreated control cell cultures.

The anti-idiotype ricin A conjugate caused 70% inhibition of protein synthesis in lipopolysaccharide stimulated spleen cells derived from mice bearing the $BCL_1$ tumor. This suggested that virtually all the $BCL_1$ cells were killed. The same conjugate caused only a 5% inhibition of normal BALB/c splenocytes. Neither NRIg coupled to ricin A chain nor anti-idiotype antibody along had any effect on either normal or tumor cells. Furthermore, the anti-idiotype ricin a chain conjugate did not inhibit protein synthesis in the T cell tumor (ASL-1) and had a marginal effect on the B cell tumor (CHI). CHI is another B-cell tumor which lacks the specific idiotypic marker expressed by the $BCL_1$ tumor.

TABLE:

| TARGET CELL: | Percent [³H] Leucine Incorporation Relative to Untreated Control | | | |
|---|---|---|---|---|
| | BALB/c | $BCL_1$ | ASL-1 | CHI |
| RABBIT ANTI-IDIOTYPE RICIN A CONJUGATE | | | | |
| 0.2 μg/ml | 90 | 28 | 100 | 74 |
| 0.25 μg/ml | | 32 | | |
| 0.5 μg/ml | 100 | 12 | | |
| 1.0 μg/ml | 100 | | | |
| NORMAL RABBIT Ig-RICIN A CONJUGATE | | | | |
| 0.2 μg/ml | 98 | 92 | 100 | 100 |
| 0.25 μg/ml | | 100 | | |
| 0.5 μg/ml | 92 | 96 | | |
| 1.0 μg/ml | 100 | | | |
| UNCONJUGATED ANTI-IDIOTYPE | | | | |
| 0.2 μg/ml | 98 | 98 | | |
| 1.0 μg/ml | 100 | 92 | | |

The above results demonstrate that ricin A chain coupled to anti-idiotype antibody inhibits protein synthesis and induces ultimate cell death in splenocytes from $BCL_1$-bearing mice to an extent consistent with the number of tumor cells originally present. These experiments further demonstrate the usefulness of anti-idiotype toxin conjugates as B cell tumor specific toxins.

EXAMPLE II

Inhibition of Protein Synthesis in Normal B Lymphocytes by an Antiμ-Ricin A Chain Conjugate Cell surface IgM is expressed on the majority of murine B lymphocytes and, therefore, represents a suitable targe for investigating the specificity of anti-isotype ricin A chain conjugates for the inhibition of protein synthesis directed against substantially all B cells.

The preparation of rabbit anti-mouse μ is prepared according to the following procedure.

Batches of 100 ml of normal mouse serum collected from outbred mice are brought to 50% saturation with ammonium sulfate, 4° C. The saturated serum samples are stirred between 4–16 hours. The precipitate was centrifuged at 10,000×g for 30 minutes and the supernatant decanted. The precipitate was dissolved in a small volume of 0.05M phosphate buffer, pH 7.6. The dissolved precipitate was dialyzed for 16–24 hours at 4° C. against 0.05M phosphate buffer with two changes of buffer during that period. 200 to 400 ml of the dissolved precipitate were chromatographed on a DEAE Sephadex-A50 column using 0.05M phosphate buffer. The first fall through peak was collected, lypholized and analyzed for purity by sodium dodecyl sulfate polyacrylamide gel electrophoresis. That peak contained mouse IgG.

New Zealand white adult rabbits were then immunized with 100 μg of purified mouse IgG emulsified in Fruend's complete adjuvant. The rabbits were reimmunized with a similar dose of antigen 4 weeks later and then bled at intervals of between 1 week and 1 year later. The rabbit bleedings were pooled and assessed for activity by Ouchterlony analysis. The antibody corresponding to anti-isotype μ was purified according to the techniques disclosed in Krolick et al, Proc. Natl. Acad. Sci. USA, 77: 5419 (1980).

Ricin A chain was isolated and then coupled to the affinity purified rabbit anti-mouse μ in the same manner as described in Example I for the preparation of anti-idiotype ricin A conjugate. The conjugate is termed anti-isotype ricin A chain.

As in Example I, the effects of anti-isotype ricin A chain conjugate on protein synthesis of lipopolysaccharide stimulate BALB/c spleen cells were investigated. Protein synthesis of all B cells was inhibited more than 80% by the anti-isotype ricin A conjugate at concentrations of 5 or 10 μg/ml. Treatment with unconjugated antibody alone had no effect.

EXAMPLE III

Inhibition of Protein Synthesis in Normal B Lymphocytes by Allotype-Specific Antiδ Ricin A Chain Conjugate The specificity of antibody-ricin A chain conjugates was investigated by further using ricin A chain conjugated to monoclonal antibodies directed against either the A or B allotype of IgD on normal B cells. These conjugates with allotype specificity should recognize only B cells bearing Igd from mouse strains expressing the corresponding allotype.

Hybridoma antibodies directed against the B allotype of mouse IgD (anti-$\delta^b$) were prepared as described in Vitetta et al., J. Immunol. 124: 2988–2990 (1980) incorporated herein by reference. Ricin A chain conjugates were then prepared with the anti-δ antibody as described in Example I. In protein inhibition experiments, the anti-allotype ricin A conjugate inhibited 95% of protein synthesis in lipopolysaccharide stimulated spleen cells obtained from C57BL-6 mice, which express the $\delta^b$ ($Ig5^b$) allotype. Lipopolysaccharide stimulated BALB/c spleen cells, which express the $\delta^a$ ($Ig5^a$) allotype, were inhibited less than 10%.

EXAMPLE IV

In Vivo Therapy of B Cell Tumor ($BCL_1$) Using Anti-Idiotype Ricin A Chain Conjugate In this study, mice bearing advanced $BCL_1$ tumors were treated by intravenous administration of tumor reactive immunotoxin. The approach was to eliminate the vast majority of the tumor burden by nonspecific cytoreductive therapy. The residual tumor cells were then killed by intravenous administration of an immunotoxin reactive with the idiotype of the surface Ig of the tumor cells. The results of these studies indicate that such immunotoxins are highly effective at inducing remissions in tumor-bearing mice provided that sufficient prior cytoreduction has been achieved.

A. The $BCL_1$ Tumor

BALB/c mice, 8–10 weeks of age, were obtained from Cumberland Farms, Clinton, TN. Mice were injected intravenously with $10^6$ $BCL_1$ cells, and therapy was begun 6–8 weeks later. At this point in time, the mice contained $1-2\times 10^9$ tumor cells in the spleens and $2-4\times 10^8$ tumor cells per ml of blood. There were also large numbers of tumor cells in the liver ($1\times 10^9$) and small numbers ($\sim$10–20%) of tumor cells in the bone marrow. Such mice would survive another 4–6 weeks in the absence of therapy. Before the initiation of therapy, the mice were staged by determining the number of $Id^+$ (BCL tumor idiotype positive) cells in the spleens and blood. This was accomplished by indirect immunofluorescent staining with rabbit anti-Id and fluorescein isothiocyanate (FITC) goat anti-rabbit Ig (GARIg). Stained cells were then quantified on the fluorescence-activated cell sorter (FACS) (FACS III; B-D FACS Systems, Becton, Dickinson & Co., Sunnyvale, CA).

B. Antibodies

ANTI-ID. Using a technique similar to that described by Levy and Dilly Proc. Natl. Acad. Sci. U.S.A. 75: 2411 producing hypoxanthine-aminopterin-thymidine sensitive myeloma cells (Sp2/0). A large portion of the hybridomas that survived the selection medium secreted Id-positive $IgM\lambda$ into the medium. One $BCL_1 \times Sp2/0$ hybridoma was recloned and then injected intraperitoneally into mineral oil-primed BALB/c mice. Large quantities of the $IgM\lambda$ were purified from the ascites by conventional chromatographic techniques. Anti-Id antibody were then generated by immunizing rabbits with the $BCL_1$ $IgM\lambda$ and removing antibodies directed against siotypic heavy and light chain determinants by adsorption on Sepharose-mouse Ig and sepharose-MOPC-104E ($\mu$, $\lambda$). As demonstrated by radioimmunoassay and immunofluorescence staining the anti-Id bound to the $BCL_1$ $IgM\lambda$ and the $BCL_1$ tumor cells but not to normal serum Ig, a panel of unrelated paraproteins, or to normal spleen cells from BALB/c mice. The anti-Id antibody was affinity purified on Sepharose bound to the $BCL_1$ $IgM\lambda$.

RABBIT ANTI-OVALBUMIN (ANTI-OVA). The serum from rabbits immunized with commercial ovalbumin was affinity purified on Sepharose-OVA. These antibodies were used as controls in all experiments and, as determined by indirect immuno fluorescence and FACS analysis, did not bind to normal spleen cells or to $BCL_1$ cells.

RABBIT ANTI-MOUSE Ig (RAMIg). Rabbit serum was prepared by immunizing rabbits with purified mouse Ig, and the specific antibody was eluted from Sepharose-mouse Ig as described previously (Isakson et al., *J. Immunol.* 125: 886 (1980). This antibody bound to both normal B cells and $BCL_1$ cells.

GOAT ANTI-RABBIT Ig (GARIg). Goats were immunized with purified rabbit IgG, and the antibody was affinity purified on Sepharose-rabbit IgG. The affinity-purified antibody was conjugated to FITC as described in Ligler et al., *J. Immunol.* 119: 1545 (1977).

C. Preparation of Immunotoxins

Antibodies were conjugated to the A chain of ricin as described above in EXAMPLE I.

D. Total Lymphoid Irradiation (TLI)

X rays were delivered by a General Electric Maxitron 300 (General Electric Co., Wilmington, MA) at a rate of 60–70 rad/minute. Mice received a total of 200 rad per treatment and a total of 8–10 treatments over a period of 8–10 days. The source-to-skin distance was 72 cm, and 2.0 mm Cu filters were used. Dosimetry was verified using a calibrating ionizing chamber and by lithium fluoride thermoluminescence dosimeter. BALB/c mice were anesthetized with nembutal at a dose of 70 $\mu$g/g body weight and were positioned in the lead apparatus described by Slavin, et al. *J. Exp. Med.* 146: 34 (1977). The major lymph nodes, thymus, and spleen were exposed to the x rays. The majority of the skull, ribs, lungs, hind legs, and tails were shielded with lead.

E. Splenectomy

TLI-conditioned mice were anesthetized with nembutal at 70 $\mu$g/g body weight. The spleens were exposed through a midline abdominal incision, the pedicle was tied off with 00 silk, and the spleens were excised. The incision was closed with metal clips. The clips were allowed to remain in place for the duration of the experiments.

F. Administration of Immunotoxin and Staging of Treated Animals

After 8–10 doses of 200 rad TLI ($\pm$splenectomy), animals were injected intraveneously with two doses of 20 $\mu$g of immunotoxin (anti-Id-Ricin A) 5–7 days apart. At weekly or biweekly intervals thereafter, mice were bled by retro-orbital punctures, and the white cell count was determined. After leukemic relapse, cells from the peripheral blood were stained with rabbit anti-Id and FITC-GARIg to confirm their tumor origin.

Results

A. Effect of TLI on Regression of the Tumor

After 8–10 fractionated doses of 200 rad TLI, the number of tumor cells in both the spleen and blood of tumor-bearing mice was reduced by 90–95%. Without further treatment, the levels of $Id^+$ cells in the spleen began to increase within a week and reached 50–80% of pretreatment levels 1–2 weeks after the termination of TLI. $Id^+$ cells were detectable in the blood 1.5–2 weeks after the completion of TLI and reached pretreatment levels 2 weeks later. The rapid relapses indicated the persistence of large numbers of tumor cells in the spleen, liver, and bone marrow.

B. Effect of Immunotoxins after TLI

Because of the rapid reappearance of tumor cells in the spleen and blood, immunotoxins were injected within several days after the completion of TLI. Although cytoreduction was optimum at this time, it was estimated that $10^8$–$10^9$ tumor cells remained in the mice. Immunotoxin (rabbit anti-Id immunotoxin specific for the $BCL_1$ tumor cells) were then injected into the TLI-conditioned mice.

The administration of immunotoxin caused a measurable delay in the reapperance of tumor cells in the spleens of the treated mice. However, by 4 weeks after treatment, these mice had relapsed with progressive $BCL_1$ disease. These experiments indicated that the administration of immunotoxin delayed relapse but that significant numbers of tumor cells escaped the effect of the immunotoxin and eventually repopulated the spleens of the treated mice.

EXAMPLE V

In Vivo Therapy of B Cell Tumor (BCL₁) Using Anti-IgD-Ricin A chain Conjugate RABBIT ANTI-MOUSE δ CHAIN (ANTI-δ). Affinity-purified rabbit anti-δ was prepared by immunizing rabbits with the TEPC-1017 (δK) paraprotein. The anti-δ antibodies were affinity purified on Sepharose-TEPC-1033 (δκ) and adsorbed with Sepharose-mouse Ig to remove all anti-light chain specificities. This anti-δ reacts with the heavy chain of cell surface IgD on both normal mouse B cells and on BCL₁ cells.

Having the experimental conditions of EXAMPLE IV in mind, TLI-conditioned mice were splenectomized two days after the completion of TLI. Post surgical survival of these mice was greater than 90%. Two days after splenectomy, mice were injected with 20 μg of anti-$δ_1$-ricin A chain immunotoxin having specificity for IgD or control anti-OVA-ricin A chain conjugate or were left untreated.

The injections were repeated 1 week later. Control mice (untreated or injected with rabbit anti-OVA-A chain) showed elevated white counts in the blood 4 weeks after the completion of TLI (and splenectomy) and died 2-3 weeks later. At the peak of leukemia, the blood cells from these mice were 70-80% Id+. In contrast, the mice treated with rabbit anti-δ-A chain showed no reemergence of leukemic cells in the blood for a period of 14 weeks after TLI, at which point the experiment was terminated.

Furthermore, peripheral blood cells were obtained from nine mice treated with rabbit anti-mouse δ-A chain at 10 weeks and again at 14 weeks after completion of TLI. The blood samples were pooled, and 0.5 ml (containing $3 \times 10^6$ cells) was injected into each of the three normal recipients. Recipients have remained tumor free for the 6 months of observation after adoptive transfer.

In comparing EXAMPLES IV and V, it is evident that one of the optimum features in successful immunotoxin therapy appears to be sufficient nonspecific cytoreduction of the tumor mass before immunotoxin administration. Similar experiments were performed with a total of 87 mice, and the average remission time after TLI, splenectomy, and anti-δ immunotoxin therapy (38 mice) was significantly greater than after nonspecific cytoreduction alone (29 mice) or nonspecific cytoreduction followed by control immunotoxin (20 mice). There were, however, instances in which late leukemic relapses were observed in mice treated with rabbit anti-mouse δ-A chain (57% of the mice relapsed). Nevertheless, in every mouse treated with the specific immunotoxin, there was a significant prolongation of remission. In three of four experiments, the mice appeared tumor free at 12-16 weeks.

Applications of the antibody-toxin conjugate of the present invention can readily be envisioned. For example, the immediate importance of the present invention is that an antibody-toxin conjugate specific for the idiotype of the surface immunoglobulin of a particular B cell tumor represents a specific toxin for that tumor. Thus, because a B cell tumor expressing a particular idiotype is of monoclonal origin, all the tumor cells expressing that idiotype are potential targets for the cytotoxic antibody-toxin conjugate. In contrast, since only a negligble number of normal B cells may express the same or cross-reacting idiotype, the overwhelming majority of B cells escape the cytotoxic effect of the anti-idiotype toxin conjugate.

A second approach to the implementation of an antibody-toxin conjugate according to the present invention involves an in vitro management of disseminated neoplasia. Heretofore, the management of patients with disseminated neoplasia involved chemotherapy and radiotherapy with autologous bone marrow rescue. In such bone marrow rescue techniques, the bone marrow is removed before the patient is treated with supralethal doses of chemotherapeutic and/or radiotherapeutic agents to kill all systemic tumor cells. The autologous bone marrow is then injected back into the patient to reconstitute the hemopoietic system. One major problem with this approach is that the bone marrow itself may contain residual tumor cells which cells will eventually regenerate a tumor within the patient. To surmount this problem of reintroducing residual tumor cells after the bone marrow rescue, the present invention involving an antibody-toxin conjugate may be applied to treat the bone marrow cells in vitro thereby eliminating the residual tumor cells. In this instance it is not critical if the normal B cells in the bone marrow are killed along with the tumor B cells because the bone marrow contains other precursor cells which can regenerate normal lymphocytic and blood cell capacity. In this instance an antibody directed against an immunoglobulin isotype coupled with a toxin may be implemented to kill all B cells present in the bone marrow including any B cell tumor also present. Afterwards the bone marrow may be reintroduced to the patient without reintroduction of any tumor cells.

A third application of using the antibody-toxin conjugates of the present invention involves the treatment of auto-immune diseases. Auto-immune disease is caused by antibodies directed against the patient's own cells, tissues or organs.

One prominent autoimmune disease is systemic lupus erythematous (SLE) [see Theophopoulos, et al, *Immunological Rev.* 55: 179-216 (1981)]. Such patients make antibodies against their own DNA, red cells, white cells, and platelets. Symptoms include high fever, skin rashes, arthritis and kidney disease. This disease is presently treated with nonspecific immunosuppressive agents such as corticosteroids or cytotoxic drugs. Nevertheless the disease is frequently fatal.

Recent studies on the pathogenesis of animal models of SLE [see Steinberg et al, *Immunological Rev.* 55: 121-154 (1981)] suggest that one of the mechanisms causing the disease is polyclonal stimulation of B lymphocytes. Thus, it appears that for reasons that are not clear there is wide spread activation of B lymphocytes causing them to produce antibodies directed against antigens termed self-antigens which normally they do not react against. Thus, one possible means of treating SLE and other autoimmune diseases (e.g., myasthenia gravis, Hashimoto's thyroiditis, etc.) would be to diminish the overactivity of the B cells.

One approach would be to use toxin coupled to antibodies against IgD. The vast majority of B cells have IgD on their surface, while there is only a small amount of IgD in the serum of most patients. Hence toxin anti-IgD conjugates will interact substantially with the majority of B cells without attacking other cells. In managing the autoimmune disease a sufficient amount of the conjugate is administered to the patient to diminish antibody formation including autoantibody formation and yet not destroy all the B cells.

Moreover, in many autoimmune diseases, particular clones of B cells form the autoantibodies. These clones produce an autoantibody that bears a particular idiotype, therefore the clones of B cells that are creating the autoantibodies bear the idiotype of the autoantibody that they secrete. [Abdou et al, *J. Clin. Invest.* 17: 1297–1304 (1981)]. Anti-idiotype antibodies against these idiotypes on the immunodominant clones could be made. Corresponding anti-idiotype-toxin conjugates could destroy the clones in question. This approach to treating autoimmune disease would be highly specific and is similar to the approach for killing B cell tumors.

The foregoing description of the invention has been directed to particular examples of antibody-toxin conjugates directed against immunoglobulins for the purposes of explanation and illustration. It is to be understood, however, that many modifications and changes in both the product and process for making the same can be made in the implementation and utilization of the present invention without departing from its concept of providing an antibody-toxin conjugate specific for immunoglobulin targets. For example, it is contemplated that toxins other than toxic polypeptides may be coupled to the antibody. Accordingly it is envisioned that radioisotopes or other carcinostatic agents such as chlorambucil, 5-fluorouracil, vincristine and various alkalating agents may be coupled to antibodies.

Accordingly, it is to be understood that the present invention admits to other embodiments and implementation in other applications and should not be construed as limiting the invention itself which is defined herein by the following claims:

What is claimed is:

1. A method of therapeutic intervention in the treatment of B cell tumors in a mammalian host exhibiting a B cell tumor, the method comprising:
    administering to said host a therapeutically effective amount of an antibody-toxin conjugate, said conjugate consisting of:
        an antibody specific for immunoglobulin isotype IgD, and one or more toxin molecules coupled to the antibody;
    the amount of antibody-toxin conjugate effective to promote B cell tumor regression.

2. The method according to claim 1 wherein the B cell tumor is leukemia.

3. The method according to claim 1 wherein the toxin is selected from the group consisting of the A chain portion of ricin, abrin, modeccin, botulina and diphtheria toxin.

4. The method according to claim 1 wherein the toxin is ricin A chain.

5. A tumor suppressive antibody-toxin conjugate selectively reactive against B cell lymphocytes bearing the immunoglobulin IgD, which consists of:
    an antibody specific for the immunoglobulin isotype IgD; and one or more toxin molecules coupled to the antibody.

6. The antibody-toxin conjugate according to claim 5 wherein the antibody is an antibody fragment selected from the group consisting of Fab, Fab', Fab'2, and Fv fragments.

7. The antibody-toxin conjugae according to claim 5 wherein the toxin is selected from the group consisting of the A chain portion of ricin, abrin, modeccin, botulina and diphtheria toxin.

8. The antibody-toxin conjugate according to claim 5 wherein the toxin is ricin A chain.

* * * * *